United States Patent [19]

Hallgren

[11] 4,096,168

[45] Jun. 20, 1978

[54] AROMATIC CARBONATES

[75] Inventor: John E. Hallgren, Scotia, N.Y.

[73] Assignee: General Electric Company, Schenectady, N.Y.

[21] Appl. No.: 731,493

[22] Filed: Oct. 12, 1976

[51] Int. Cl.$^2$ ............................................. C07C 68/00
[52] U.S. Cl. ................................ 260/463; 260/47 XA
[58] Field of Search ........................... 260/463, 47 XA

[56] References Cited

U.S. PATENT DOCUMENTS

| | | | |
|---|---|---|---|
| 3,114,762 | 12/1963 | Mador et al. | 260/463 |
| 3,846,468 | 11/1974 | Perrotti et al. | 260/463 |

OTHER PUBLICATIONS

P. P. Borisov et al., Chem. Abstracts, 32:2414; Apr.–Jun. 1938.

*Primary Examiner*—Elbert L. Roberts
*Assistant Examiner*—Molly C. Eakin
*Attorney, Agent, or Firm*—F. W. Turner; J. T. Cohen; M. Snyder

[57] ABSTRACT

An aromatic carbonate process comprising contacting a phenol, carbon monoxide, a base, a Group VIIIB element selected from ruthenium, rhodium, palladium, osmium, iridium or platinum having an oxidation state of plus one. The resulting aromatic mono- and polycarbonates are useful in the preparation of polycarbonates or as polycarbonates, per se, respectively, which can be molded or formed into films, sheets, fibers, laminates or reinforced plastics by conventional techniques.

23 Claims, No Drawings

AROMATIC CARBONATES

CROSS-REFERENCE TO RELATED APPLICATIONS

This invention is related to my copending U.S. patent application Ser. Nos. 731,443 and 731,494, filed concurrently herewith and Alan J. Chalk's U.S. patent application Ser. Nos. 731,496 and 731,495 filed concurrently herewith. All of the aforesaid applications are assigned to the same assignee as the assignee of this application.

BACKGROUND OF THE INVENTION

1. Field of the Invention

This invention relates to an aromatic carbonate process comprising contacting a phenol, carbon monoxide, a base, a Group VIIIB element selected from ruthenium, rhodium, palladium, osmium, iridium or platinum having an oxidation state of plus one.

2. Description of the Prior Art

A. J. Chalk recognized — as broadly disclosed in the Chalk patent applications referenced herein — that aromatic carbonates can be prepared by contacting a phenol, carbon monoxide, a base, and a Group VIIIB element selected from ruthenium, rhodium, palladium osmium, iridium or platinum having an oxidation state greater than zero.

Unexpectedly, I have found that when a Group VIIIB element is employed at the first oxidation level greater than zero at the beginning of my aromatic carbonate process that the yields of aromatic carbonate are optimized and that by-product undesirable side reactions such as the formation of aromatic salicylates are essentially or substantially avoided.

DESCRIPTION OF THE INVENTION

This invention embodies an aromatic carbonate process comprising contacting a phenol, carbon monoxide, a base, and a Group VIIIB element selected from ruthenium, rhodium, palladium, osmium, iridium or platinum having an oxidation state of plus one.

The reactants and the resulting reaction products of my process can be illustrated by the following general equations which are furnished for illustrative purposes only since the reaction mechanisms involved in the preparation of aromatic monocarbonates (Eq. 1) and polycarbonates (Eq. 2) may be much more complex:

$$2n\text{Pd(CO)Cl} + 2n\text{R'OH} + 2n\text{R}_3\text{N} \rightarrow 2n\text{Pd}^\circ + n\text{R'}_2\text{CO}_3 + 2n\text{R}_3\text{N}^+\text{H Cl}^- \quad \text{Eq. 1}$$

Eq.2  $2n\text{Pd(CO)Cl} + (n + 1)\text{R''}(\text{OH})_2 + 2n\text{R}_3\text{N}$

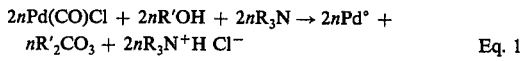

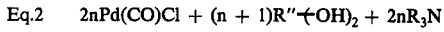

wherein R is an alkyl radical (including cycloalkyl), R' is an aryl radical, R" is an arene radical, and n is a number equal to at least 1.

Any of the phenols, solvents, bases, ligands or reaction parameters relative to time, temperature and pressure disclosed in A. J. Chalk's copending 731,496 application referenced herein can be employed. Accordingly, their descriptions are hereby incorporated herein in their entirety by reference. Also, any of the amounts disclosed in the aforementioned A. J. Chalk 731,496 application can also be employed in a like manner and accordingly the definition of the amounts are also incorporated herein in their entirety also by reference.

The Group VIIIB element that can be employed is defined herein and in the appended claims as "the Group VIIIB element" and is any Group VIIIB element subject to the proviso that it is selected from ruthenium, rhodium, palladium, osmium, iridium or platinum having an oxidation state of plus one, i.e. a first oxidation level greater than zero. The Group VIIIB element can be present in ionic, inorganic or organic compound or complex, etc. form. The Group VIIIB element can be employed in any form, e.g. oxide, halide, nitrate, sulfate, oxalate, acetate, carbonate, propionate, hydroxide or tartrate form, etc.

The Group VIIIB elements can be employed in complex form, e.g. with ligands, such as carbon monoxide, nitriles, tertiary amines, phosphines, arsines, or stibenes, etc. Illustratively the complex forms are often represented by those skilled in the art as mono-, di-, or polynuclear forms. Generally, the dimeric or polymeric forms are considered to contain the Group VIIIB atoms bridged by ligands, halogens, etc. Preferably the Group VIIIB elements take the form of a homogeneous admixture, more preferably a homogeneous solution, when combined with the phenolic reactants, especially when the process is carried out under liquid phase reaction conditions.

Illustrative of the generally preferred Group VIIIB element compounds or complexes that can be used in my process follow: Ru(CO)Cl, Ru(CO)Br, Ru(CO)I, RuCl[P(C$_2$H$_5$)$_3$]$_3$, etc.; RhCl(CO)[P(C$_2$H$_5$)$_3$]$_2$, RhCl(CO)(CNCH$_3$OC$_6$H$_4$)$_2$, [Rh(CNCH$_3$OC$_6$H$_4$)$_4$]Cl, [Rh(CNClC$_6$H$_4$)$_4$]Cl, [Rh(CO)$_2$Cl]$_2$, Rh$_2$Cl$_2$(CO)$_2$, Rh$_2$(CO)$_4$Cl$_2$, Rh$_2$(CO)$_4$Br$_2$, Rh$_2$(CO)$_4$I$_2$, etc.; Pd(CO)Cl, Pd(CO)Br, Pd(CO)I, PdH(CO)Cl, PdH(CO)Br, Pd(C$_6$H$_6$)(H$_2$O)ClO$_4$, Pd$_2$(CO)$_2$Cl, [(H$_9$C$_4$)$_4$N]$_2$PdBr$_4$, K$_2$Pd$_2$(CO)$_2$Cl$_4$, Na$_2$Pd$_2$(CO)$_2$Br$_4$, etc.; Os(CO)$_2$Cl, Os(CO)$_2$Br, Os(CO)$_2$I, Os(CO)$_4$Cl, Os(CO)$_4$Br, Os(CO)$_4$I, etc.; Ir(CO)$_2$Cl, Ir(CO)$_2$Br, Ir(CO)$_2$I, Ir(CO)$_3$Cl, Ir(CO)$_3$Br, Ir(CO)$_3$I, IrCl(CO)[P(C$_6$H$_5$)$_3$]$_2$, etc.; and Pt(CO)Cl, Pt(CO)Br, Pt(CO)I, Na$_2$Pt$_2$(CO)$_2$Cl$_4$, Na$_2$Pt$_2$(CO)$_2$Br$_4$, K$_2$Pt$_2$(CO)$_2$I$_4$, etc.

The Group VIIIB element compounds and/or complexes can be prepared by any method well-known to those skilled in the art including the methods referenced in

*Reactions of Transition-Metal Complexes*, J. P. Candlin, K. A. Taylor and D. T. Thompson, Elsevier Publishing Co. (1968) Library of Congress Catalog Card No. 67-19855, among others as well as those described in U.S. and foreign technical journals and patents.

In my process, preferred phenolic reactants are phenols containing from 6 to 30, and more preferably from 6 to 15 carbon atoms. Illustrative of commercially important phenolic reactants included within the above description are the following: phenol itself (hydroxy benzene), napthol, ortho-, meta-, or paracresol, catechol, cumenol, xylenol, resorcinol, the various isomers of dihydroxydiphenyl, the isomers of dihydroxynaphthalene, bis(4-hydroxyphenyl)propane-2,2,α,α'-bis(4-hydroxyphenyl)-p-diisopropylbenzene, 4,4'-dihydroxy-3,5,3',5'-tetrachlorophenylpropane-2,2,4,4'-dihydroxy-3,5,3',5'-tetrachloro-phenylpropane-2,2 and 4,4'-dihydroxy-3,5,3',5'-tetrachloro-phenylpropane-2,2 and 4,4'-dihydroxy-3,5,3',5'-tetrabromo-phenylpropane-2,2, chloroglucinol, dihydroxy oligomers, for example an oligomer derived from bisphenol-A, etc.

In my process, preferred bases included sterically hindered amines, e.g. diisopropylmonoethylamine, 2,2,6,6-N-pentamethylpiperidine, etc.

Any amount of Group VIIIB element can be employed. For example, Group VIIIB element to phenol mole proportions within the range of from about 0.001:1 or lower to about 1000:1 or higher are effective, however, preferably ratios of from 0.1:1 to 10:1, and more preferably at least 1:1 are employed in order to insure that optimum conversion of the phenol to aromatic carbonate occurs.

Any amount of carbon monoxide can be employed. Preferably the process is carried out under positive carbon monoxide pressure, i.e., where carbon monoxide is present in stoichiometric amounts sufficient to form the desired aromatic mono- or polycarbonate. In general, carbon monoxide pressures within the range of from about ½ to about 500 atmospheres, or even higher, can be employed with good results. Presently preferred are CO pressures within the range of from 1 to 200 atmospheres.

Any reaction time or temperature can be employed.

Following the procedures of my invention described herein, aromatic carbonates are formed in the substantial absence of aromatic salicylates, i.e. aromatic salicylates being present in amounts which cannot be analytically determined according to the procedures described or employed herein in the analysis of the resulting aromatic carbonate reaction products.

In order that those skilled in the art may better understand my invention, the following examples are given which are illustrative of the best mode of this invention, however, these examples are not intended to limit the invention in any manner whatsoever. In the examples, unless otherwise specified, all parts are by weight and the reaction products were verified by infrared spectrum, C-13 nuclear magnetic resonance and mass spectrometry.

EXAMPLE I

Preparation of diphenyl carbonate using phenol, also known as hydroxybenzene, carbon monoxide, diisopropylmonoethylamine and poly[palladium(I) monocarbonyl chloride].

Polypalladium(I) monocarbonyl chloride was prepared by modification of the literature procedure of W. Schnabel and E. Kober, J. Organomet. Chem. 19, 455 (1969). The procedure involved the addition of 0.77 g. (2.0 mmol.) of bis(benzonitrile)palladium(II) dichloride to 200 ml. of chloroform. Carbon monoxide was passed through the resulting solution slowly until a yellow precipitate formed and the color of the organic phase was discharged. The mixture was filtered and the precipitate dried at room temperature in vacuo. Subsequent work-up and analysis showed the presence of 0.24 g. (72% yield) of poly[palladium(I) monocarbonyl chloride] of the empirical formula poly[Pd(CO)Cl]. A mixture containing the amount of 0.094 g. (1.0 mmol.) of phenol, 0.26 g. (2.0 mmol.) of diisopropylmonoethylamine and 0.24 g. of palladium(I) monocarbonyl chloride was saturated with carbon monoxide and a black precipitate formed. GC analysis of the reaction mixture showed the presence of 0.11 g. (96% yield) of diphenyl carbonate of the formula:

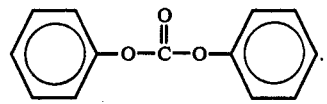

EXAMPLE II

Preparation of 4,4'-dimethyldiphenyl carbonate using 4-cresol as the phenolic reactant.

A vessel was charged with 0.30 g. (1.8 mmol.) of poly[Pd(CO)Cl] prepared in accord with the procedure of Example I above, 0.383 g. (3.54 mmol.) of 4-cresol, 0.46 g. (3.54 mmol.) of diisopropylmonoethylamine and 5 ml. of methylene chloride. The reaction procedure described in Example I was followed. Subsequent work-up and analysis showed the presence of 0.13 g. (62% yield) of bis-p-tolyl carbonate, also known as 4,4'-dimethyldiphenyl carbonate, of the formula:

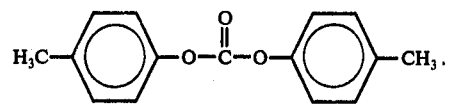

EXAMPLE III

Preparation of bis(α,α-dimethylbenzyl)diphenyl carbonate using p-cumylphenol as the phenolic reactant.

0.26 g. (1.53 mmol.) of poly[Pd(CO)Cl], poly[palladium (I) monocarbonyl chloride] prepared as in Example I, 0.65 g. (3.06 mmol.) of p-cumylphenol, 0.40 g. (3.06 mmol.) of diisopropylmonoethylamine and 10 ml. of methylene chloride were contacted with carbon monoxide as described in Example I. Subsequent work-up and analysis showed the presence of 0.59 g. (86% yield) of bis(p-cumyl-phenyl)carbonate also known as 4,4'-(α,α-dimethylbenzyl)diphenyl carbonate, of the formula:

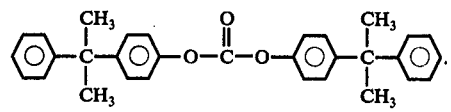

EXAMPLE IV

Preparation of 4,4'-dichlorodiphenyl carbonate using 4-chlorophenol as the phenolic reactant.

0.26 g. (1.53 mmol.) of poly[Pd(CO)Cl], 0.39 g. (3.06 mmol.) of p-chlorophenol, 0.39 g. (3.06 mmol.) of diisopropylmonoethylamine and 5 ml. of methylene chloride were contacted with carbon monoxide as described in Example I. Subsequent work-up and analysis showed the presence of 0.151 g. (35% yield) of bis-(p-chlorophenyl) carbonate, also known as 4,4'-dichlorodiphenyl carbonate, of the formula:

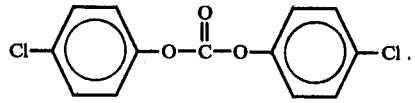

EXAMPLE V

Preparation of 4,4'-dimethoxydiphenyl carbonate using p-methoxy phenol as the phenolic reactant.

0.31 g. (1.8 mmol.) poly[Pd(CO)Cl], 0.45 g. (3.6 mmol.) of p-methoxyphenol, 0.47 g. (3.6 mmol.) of diisopropylmonoethylamine in methylene chloride were contacted with carbon monoxide as described in Example I. Subsequent work-up and analysis showed the presence of 0.11 g. (45% yield) of bis(p-methoxyphenyl)carbonate, also known as 4,4'-dimethoxydiphenyl carbonate, 0.09 g. (40% yield) of 4,4'-dimethoxy-2,2'-bisphenol, and 0.02 g. (10% yield) of 4-methoxy-2,6-bis(2-hydroxy-5-methoxyphenyl)phenol of the formulas, respectively:

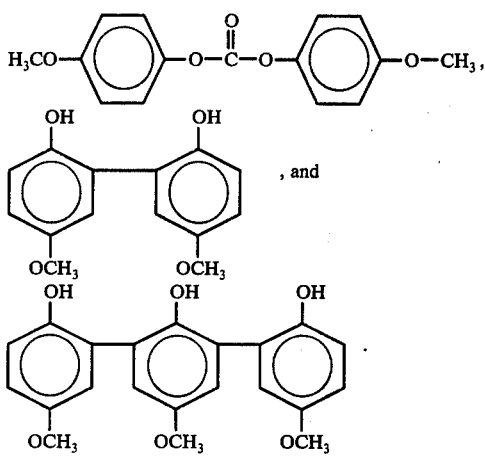

EXAMPLE VI

Preparation of p-cumylphenyl(phenyl) carbonate and bis(p-cumylphenyl) carbonate using a mixture of p-cumylphenol and phenol as the phenolic reactants.

0.31 grams (1.8 mmol.) of poly[Pd(CO)Cl], 0.39 g. (1.82 mmol.) of p-cumylphenol, 0.17 g. (1.8 mmol.) of phenol, 6 ml. of methylene chloride, 0.47 g. (3.64 mmol.) of diisopropylmonoethylamine were saturated with carbon monoxide during 3-hour reaction period. Subsequent work-up and analysis showed the presence of 0.19 grams (45% yield) of bis(p-cumylphenyl) carbonate and 0.14 (45% yield) of p-cumylphenyl(phenyl) carbonate and a trace (estimated 2% yield) of diphenyl carbonate.

EXAMPLE VII

Preparation of bis(p-cumylphenyl) carbonate and p-cumylphenyl)p-chlorophenyl) carbonate using a mixture of p-cumylphenol and p-chlorophenol as the phenolic reactants.

0.20 grams (1.2 mmol.) of poly[Pd(CO)Cl], 0.25 g. (1.2 mmol.) of p-cumylphenol, 0.15 grams (1.2 mmol.) of p-chlorophenol, 0.30 g. (2.36 mmol.) of diisopropylmonoethylamine and 3 ml. of methylene chloride were contacted with carbon monoxide as in Example I. Subsequent work-up and analysis showed the presence of 0.11 grams (3% yield) of bis(p-cumylphenyl) carbonate and 0.088 grams (40% yield) of p-cumylphenyl(p-chlorophenyl) carbonate.

EXAMPLE VIII

Preparation of a mixture of bis(p-methoxyphenyl) carbonate, 4,4'-dimethoxy-2,2'-bisphenol and p-cumylphenyl(p-methoxyphenyl) carbonate by contacting a mixture of p-cumylphenol and p-methoxyphenol with carbon monoxide carried out in the presence of poly[Pd(CO)Cl].

0.17 grams (1.0 mmol.) of [Pd(CO)Cl], 0.42 g. (2.0 mmol.) of p-cumylphenyl, 0.24 g. (2.0 mmol.) of p-methoxyphenol, 0.52 g. (4.0 mmol.) of diisopropylmonoethylamine, and 5 ml. of methylene chloride were contacted with carbon monoxide as in Example I. Subsequent work-up and analysis showed the presence of 0.03 g. (25% yield) of bis(p-methoxyphenyl) carbonate, 0.05 g. (25% yield) of 4,4'-dimethoxy-2,2'-bisphenol, and 0.055 g. (50% yield) of p-cumylphenyl(p-methoxyphenyl) carbonate.

EXAMPLE IX

Preparation of a polycarbonate of bisphenol-A by contacting bis(4-hydroxyphenyl)propane-2,2, carbon monoxide, diisopropylmonoethylamine and poly[palladium(I) monocarbonyl chloride].

A 50 ml. 4-neck resin kettle fitted with a gas addition type hollow turbine stirrer, septum cap and gas outlet was charged with 5.15 g. (0.030 mol.) of poly[palladium(I) monocarbonyl chloride] of the empirical formula [Pd(CO)Cl]$_x$, 3.29 g. (0.014 mol.) of bisphenol-A and 25 ml. of methylene chloride. Carbon monoxide was bubbled through the resulting slurry and 7.84 g. (0.061 mol.) of diisopropylmonoethylamine was added. The reaction mixture turned black immediately. Passage of the carbon monoxide through the reaction media was continued for about 15 hours. The resulting reaction products were filtered, the filtrate was concentrated and precipitated by addition to 300 ml. of vigorously stirred methanol. The resulting polymer was collected by filtration, redissolved, filtered and reprecipitated. Polymer was dried overnight in vacuo at 100° C. Gel permeation chromotography (GPC) analysis of the reaction mixture showed the presence of a polycarbonate of bisphenol-A containing recurring units of the formula:

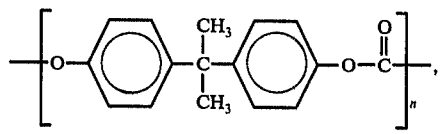

wherein n is an integer averaging at least about 6. A resume of reaction conditions and products describing phenolic reactant, bisphenol (—OH) group to palladium mole ratio, yield of polycarbonate on a weight basis, $\overline{M}_n$ number average molecular weight, $\overline{M}_w$ weight average molecular weight, $\overline{M}_w/\overline{M}_n$, $\overline{n}$ = average degree of polymerization is set out in Table I which follows:

TABLE I

| Phenolic Reactant | Mole Ratio OH:Pd | Yield (wt./%) | $\overline{M}_n$ | $\overline{M}_w$ | $\overline{M}_w/\overline{M}_n$ | $\overline{n}$ |
|---|---|---|---|---|---|---|
| BPA[1] | 1.0 | 5[2] | 1714[3] | 2053[3] | 1.20[3] | 6 |

[1]bisphenol-A
[2]% recovered by weight after precipitation of a 5% CH$_2$Cl$_2$ solution into methanol
[3]GPC data using polystyrene standards in CH$_2$Cl$_2$

EXAMPLE X

Preparation of a polycarbonate of bisphenol-A using a monocarbonate oligomer of bis(4-hydroxyphenyl)propane-2,2 as the phenolic reactant.

The preparations of the poly[palladium(I)monocarbonyl chloride] and the polycarbonate were conducted as set out in Examples I and IX, respectively, except as noted hereafter. The reaction medium contained 0.076 g. (0.45 mmol.) of poly[palladium(I)monocarbonyl chloride], 0.087 g. (0.18 mmol.) of bisphenol-A monocarbonate, 3 ml. of methylene chloride and 0.12 g. (0.90 mmol.) of diisopropylmonoethylamine. GPC analysis of the reaction product mixture determined the presence of a polycarbonate of bisphenol-A containing recurring units of the Example IX formula. A resume of the reaction is set out in Table II which follows:

TABLE II

| Phenolic Reactant | Mole Ratio OH:Pd | Yield (wt./%) | $\overline{M}_n$ | $\overline{M}_w$ | $\overline{M}_w/\overline{M}_n$ | $\overline{n}$ |
|---|---|---|---|---|---|---|
| BPA—C(=O)—BPA[1] | 0.8 | 50[2] | 1773[3] | 2501[3] | 1.41[3] | 6 |

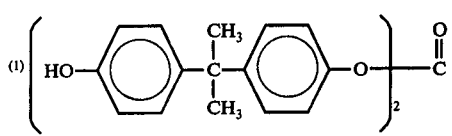

[2] & [3] as in Example IX, Table I

EXAMPLE XI

Preparation of a polycarbonate of bisphenol-A using 2,2,6,6,N-pentamethylpiperidine as a base.

The preparations of the poly[palladium(I)monocarbonyl chloride] and the polycarbonate were conducted as set out in Examples I and IX, respectively, except as noted hereafter. The reaction medium contained 2.669 g. (15.71 moles) of poly[palladium(I)monocarbonyl chloride], 1,345 g. (5.89 mmol.) of bisphenol-A, 15 ml. of methylene chloride and 3.659 g. (23.56 mmol.) of 2,2,6,6,N-pentamethylpiperidine. The reaction products were concentrated in 100 ml. of methanol and dried at 80° C. GPC analysis of the reaction mixture show the presence of 1.42 g. (95% yield) of a polycarbonate of bisphenol-A containing the recurring units of the Example IX formula. A resume of the reaction is set out in Table III.

TABLE III

| Phenolic Reactant | Mole Ratio OH:Pd | Yield (wt./%) | $\overline{M}_n$ | $\overline{M}_w$ | $\overline{M}_w/\overline{M}_n$ | $\overline{n}$ |
|---|---|---|---|---|---|---|
| Bisphenol-A[1] | 0.75 | 95[2] | 5000[3] | 9000[3] | 1.8[3] | 20 |

[1] & [2] as in Example IX, Table I
[3] GPC data using polycarbonate standards in tetrahydrofuran

EXAMPLE XII

Preparation of a polycarbonate of bisphenol-A using poly[palladium(I)monocarbonyl bromide].

The preparations of poly[palladium(I)monocarbonyl bromide] and the polycarbonate were conducted as set out in Examples I and IX, respectively, except as noted hereafter.

The poly[palladium(I)monocarbonyl bromide] procedure involved the use of 0.77 g. (2.0 mmol.) of bisbenzonitrile palladium(II) dibromide, and resulted in a 49% yield of poly[palladium(I)monocarbonyl bromide]. The reaction medium contained 2.00 g. (9.3 moles) of poly[palladium(I) monocarbonyl bromide], 0.96 g. (4.2 mmol.) of bisphenol-A, 20 mkl. of methylene chloride and 2.89 g. (18.6 mmol.) of 2,2,6,6,N-pentamethylpiperidine. The reaction products ml. concentrated in 100 ml. of methanol and dried at 60° C. GPC analysis showed the presence of 0.97 g. (91% yield) of a polycarbonate of bisphenol-A containing the recurring units of the Example IX formula. A resume of the reaction is set out in Table IV.

TABLE IV

| Phenolic Reactant | Mole Ratio OH:Pd | Yield (wt./%) | $\overline{M}_n$ | $\overline{M}_w$ | $\overline{M}_w/\overline{M}_n$ | $\overline{n}$ |
|---|---|---|---|---|---|---|
| Bisphenol-A[1] | 0.9 | 91[2] | 8000[3] | 16,000[3] | 2.0[3] | 32 |

[1] & [2] as in Example IX, Table I
[3] as in Example VI, Table III

EXAMPLE XIII

Preparation of a polycarbonate of bisphenol-A using the polycarbonate product of Example XII as the phenolic reactant.

The preparations of the poly[palladium(I) monocarbonyl chloride] and the polycarbonate was conducted as set out in Examples I and IX, respectively, except as noted hereafter. The reaction medium contained 0.086 grams, (0.40 mmol.) of poly[palladium(I) monocarbonyl chloride], 0.500 grams of the polycarbonate product of Example XII, 16 ml. of methylene chloride and 0.124 g. (0.80 mmol.) of 2,2,6,6,N-pentamethylpiperidine. The reaction products were concentrated in 100 ml. of methanol and dried at 80° C. GPC analysis showed the presence of 0.43 g. (86% yield) of a polycarbonate of bisphenol-A containing the recurring units of the Example IX formula. A resume of the reaction is set out in Table V:

TABLE V

| Phenolic Reactant | Mole Ratio OH:Pd | Yield (wt./%) | $\overline{M}_n$ | $\overline{M}_w$ | $\overline{M}_w/\overline{M}_n$ | $\overline{n}$ |
|---|---|---|---|---|---|---|
| Bisphenol-A[1] | n.d. | 86[2] | 11,000[3] | n.d. | n.d. | 44 |

[1] polycarbonate of bisphenol-A of Example XII
[2] & [3] as in Example IX, Table I
n.d. not determined As illustrated by the preparation of polycarbonates of bisphenol-A in Examples IX to XIII above, in general the aromatic polycarbonates that can be prepared by my process are oligomeric or polymeric and have an intrinsic viscosity range of as high as 1.5 or even higher deciliters per gram (dl./g.) as measured in methylene chloride. Especially useful are polycarbonate resins which are generally suited to the preparation of films, sheets, fibers, laminates or reinforced plastics (e.g. for insulating or protective coating applications) by conventional techniques which have an intrinsic viscosity of from about 0.35 to about 0.7 dl./g.

EXAMPLE XIV

Preparation of diphenylcarbonate using bis(tetrapropylammonium)dicarbonyl tetrachloroplatinite(I).

The bis(tetrapropylammonium)dicarbonyl tetrachloroplatinite(I) was prepared by the procedure of Goggin and Goodfellow, J. Chem. Soc. (Dalton) (1973) 2355. The reaction vessel was charged with 0.48 g. (0.5 mmol.) of bis(tetrapropylammonium)dicarbonyl tetrachloroplatinite(I), 0.38 g. (4.0 mmol.) of phenol, and 7 ml. of methylene chloride. Carbon monoxide was bubbled through the mixture and 0.62 g. (4.0 mmol.) of 2,2,6,6-N-pentamethylpiperidine was added. Subsequent work and analysis showed the presence of diphenylcarbonate estimated at a 2% yield.

As illustrated by the foregoing Examples, aromatic carbonates are readily formed in the substantial absence of aromatic salicylates wherein the Group VIIIB element is employed in an oxidation state of plus one prior to forming a reaction mixture containing any of the other reactants. These examples illustrate one of preferred methods, i.e. a "best mode", of practicing my invention.

Further, another process parameter of my invention comprises using a controlled reaction process sequence whereby an aromatic carbonate is readily formed in the substantial absence of an aromatic salicylate wherein the Group VIIIB employed at the beginning of the aromatic carbonate process has an oxidation state greater than plus one. This process requires a carbonate preliminary reaction admixture, i.e. "carbonate PRM" containing a phenolic reactant and a Group VIIIB element having an oxidation state greater than plus one, be contacted with carbon monoxide for a substantial period of time, e.g. 5, 10, 20, 60 or more minutes, prior to the addition of a base thereto.

EXAMPLES XV -XVIII

Preparation of diphenylcarbonate using a carbonate preliminary reaction admixture, i.e. phenol, carbon monoxide and bis(benzonitrile)palladium(II)dichloride and regulating relative to time the order of addition of a base, e.g. diisopropylmonoethylamine, to the preliminary reaction admixture.

A series of independent reactions were carried out wherein a preliminary reaction admixture, i.e. a "PRM", was contacted with a base, i.e. diisopropylmonoethylamine, 5, 20, 60 and 120 minutes after the PRM was initially contacted with carbon monoxide. A control run was carried out with base being added at zero minutes, e.g. essentially simultaneously with the formation of the PRM. Three hours after the combination of the PRM ingredients, the resulting reaction products were analyzed and the relative proportions of diphenylcarbonate and phenylsalicylate were determined. Summarized in Table I are the reaction parameters and products, i.e. the time of addition of the base to the PRM and the resulting reaction products, i.e. the diphenylcarbonate and the phenylsalicylate.

TABLE I

| Example No. | Run No. | Base Addition Time (min) | Relative Proportions diphenylcarbonate:phenylsalicylate |
|---|---|---|---|
| Control | 1.* | 0 | 0.05 : 99.95 |
| XV | 2. | 5 | 0.25 : 99.75 |
| XVI | 3. | 20 | 5 : 95 |
| XVII | 4. | 60 | 50 : 50 |
| XVIII | 5. | 120 | 100 : 0 |

*-control run

As illustrated by this example, the time and "order of addition" sequence, i.e. time and order of addition of base to a carbonate PRM in the practice of my process significantly effects the relative proportions and accordingly the yield of diphenylcarbonate.

In the practice of my process, the Group VIIIB elements after separation from the resulting reaction products can be oxidized to any suitable oxidation state, and can be reemployed, that is, recycled in the aromatic carbonate process described herein.

Although the above examples have illustrated various modifications and changes that can made in the carrying out of my process, it will be apparent to those skilled in the art that other Group VIIB metals, phenolic compounds, ligands, oxidants, redox components, drying agents and solvents as well as other reaction conditions can be effected without departing from the scope of the invention.

I claim:

1. An improved aromatic carbonate process wherein an aromatic carbonate is formed in the substantial absence of an aromatic salicylate which comprises contacting a phenol with carbon monoxide, a base, and a Group VIIIB element selected from ruthenium, rhodium, palladium, iridium, osmium or platinum having an oxidation state of plus one.

2. The claim 1 process, wherein said element is present in an ionic form.

3. The claim 1 process, further comprising contacting a Group VIIIB element selected from ruthenium, rhodium, palladium, osmium, iridium, or platinum having an oxidation state of at least ×2 with carbon monoxide and a phenol, prior to contacting the resulting admixture with a base.

4. The claim 1 process, wherein said base is a sterically hindered amine.

5. The claim 1 process, wherein said element is associated with a carbonyl group.

6. The claim 1 process, wherein said element is associated with a halide.

7. The claim 1 process, wherein said element is associated with an inorganic halide compound.

8. The claim 1 process, wherein methylene chloride is employed as a solvent, the base is diisopropylmonoethylamine, the phenol is a phenol, and Group VIIIB element is polypalladium(I)monocarbonyl chloride.

9. The claim 1 process, wherein methylene chloride is employed as a solvent, the base is diisopropylmonoethylamine, the phenol is bis(4-hydroxyphenyl)propane-2,2 and the Group VIIIB element is polypalladium(I)monocarbonyl chloride.

10. The claim 1 process, wherein methylene chloride is employed as a solvent, the base is 2,2,6,6,N-pentamethylpiperidine the phenol is bis(4-hydroxyphenyl)propane-2,2, the Group VIIIB element is polypalladium(I)monocarbonyl bromide.

11. The claim 1 process, wherein methylene chloride is employed as a solvent, the base is 2,2,6,6,N-pentamethylpiperidine, the phenol is a phenol, the Group VIIIB element is platinum in the form of bis(tetrapropylammonium)dicarbonyltetrachloroplatinite(I).

12. The claim 1 process, further comprising, after the preparation of the aromatic carbonate, separating at least a portion of any resulting Group VIIIB element or compound from said carbonate, oxidizing at least a portion of said resulting Group VIIIB element or compound to an oxidation state greater than zero, and recycling at least a portion of said oxidized element in said aromatic carbonate process.

13. An improved aromatic polycarbonate process wherein an aromatic polycarbonate is formed in the substantial absence of an aromatic salicylate which comprises contacting an aromatic polyphenol with carbon monoxide in the presence of a base and a Group VIIIB metal selected from the class consisting of ruthenium, rhodium, palladium, osmium, iridium and platinum having an oxidation state of plus one.

14. An improved aromatic polycarbonate process wherein an aromatic polycarbonate is formed in the substantial absence of an aromatic salicylate which comprises contacting an aromatic bisphenol of the formula:

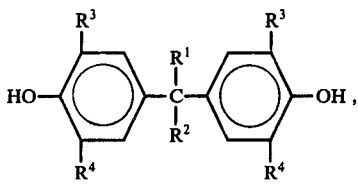

where independently each $R^1$ and $R^2$ is hydrogen, $C_{1-4}$ alkyl or phenyl and independently each $R^3$ and $R^4$ is hydrogen or $C_{1-4}$ alkyl, with carbon monoxide in the presence of a base and a Group VIIIB metal selected from the class consisting of ruthenium, rhodium, palladium, osmium, iridium and platinum having an oxidation state of plus one.

15. The claim 14 process, wherein $R^1$ and $R^2$ are methyl and at least one of $R^3$ and $R^4$ is hydrogen.

16. The claim 15 process, wherein the base is a tertiary amine.

17. The claim 16 process, carried out in the presence of an inert solvent.

18. An improved aromatic polycarbonate process wherein a polycarbonate is formed in substantial absence of an aromatic salicylate which comprises contacting an aromatic bisphenol of the formula:

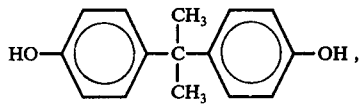

with carbon monoxide in the presence of a base and a Group VIIIB metal selected from the class consisting of ruthenium, rhodium, palladium, osmium, iridium and platinum having an oxidation state of plus one.

19. An improved aromatic monocarbonate process wherein an aromatic monocarbonate is formed in substantial absence of an aromatic salicylate which comprises contacting an aromatic phenol of the formula:

$$R_a(OH)_x,$$

where $R_a$ represents an aromatic radical wherein the -OH radical is attached directly to an aromatic ring carbon atom and x is the number 1, with carbon monoxide, a base, and a Group VIIIB element selected from the class consisting of ruthenium, rhodium, palladium, osmium, iridium and platinum having an oxidation state of plus one.

20. The claim 19 process, wherein $R_a$ is selected from carbo- or heteromonocyclic, polycyclic or fused polycyclic radicals.

21. The claim 20 process, wherein the base is a tertiary amine.

22. The claim 21 process, carried out in the presence of an inert solvent.

23. An improved aromatic monocarbonate process wherein an aromatic monocarbonate is formed in substantial absence of an aromatic salicylate which comprises contacting a phenol of the formula:

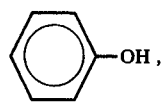

with carbon monoxide, a base, and a Group VIIIB element selected from the class consisting of ruthenium, rhodium, palladium, osmium, iridium and platinum having an oxidation state of plus one.

* * * * *